(12) United States Patent
Hsu et al.

(10) Patent No.: US 8,308,351 B2
(45) Date of Patent: Nov. 13, 2012

(54) APPARATUS FOR MEASURING THE TEMPERATURE COEFFICIENT OF A CONCENTRATOR PHOTOVOLTAIC MODULE

(75) Inventors: Yi-Ru Hsu, Kinmen (TW); Tsung-Te Lin, Knohsiung (TW); Chii-Neng Ou Yang, Taoyuan (TW); Cheng-Ban Chung, Taichung (TW); Yao-Tung Hsu, Taoyuan (TW)

(73) Assignee: Atomic Energy Council-Institute of Nuclear Energy Research, Lungtan, Taoyuan (TW)

( * ) Notice: Subject to any disclaimer, the term of this patent is extended or adjusted under 35 U.S.C. 154(b) by 472 days.

(21) Appl. No.: 12/705,033

(22) Filed: Feb. 12, 2010

(65) Prior Publication Data
US 2011/0103423 A1 May 5, 2011

(30) Foreign Application Priority Data

Oct. 30, 2009 (TW) .................................. 098136795

(51) Int. Cl.
*G01N 25/20* (2006.01)
*G01K 1/08* (2006.01)
*G01K 1/14* (2006.01)
*G01K 13/00* (2006.01)

(52) U.S. Cl. .......... 374/43; 374/208; 374/141; 374/149; 374/152

(58) Field of Classification Search ............ 374/43, 374/208, 141, 149, 152
See application file for complete search history.

(56) References Cited

U.S. PATENT DOCUMENTS

| 4,817,447 A * | 4/1989 | Kashima et al. ............. 73/865.6 |
| 2002/0014886 A1* | 2/2002 | Matsuyama ..................... 324/96 |
| 2007/0227585 A1* | 10/2007 | Yoshimine .................... 136/251 |
| 2009/0179651 A1* | 7/2009 | Elgar et al. .................... 324/501 |
| 2009/0223511 A1* | 9/2009 | Cox .............................. 126/714 |
| 2010/0046575 A1* | 2/2010 | Hebert et al. ................... 374/57 |
| 2011/0186109 A1* | 8/2011 | Elazari ......................... 136/248 |
| 2012/0174982 A1* | 7/2012 | Tsunomura et al. .......... 136/259 |

* cited by examiner

*Primary Examiner* — Mirellys Jagan
(74) *Attorney, Agent, or Firm* — Jackson IPG PLLC

(57) ABSTRACT

Disclosed is an apparatus for measuring temperature coefficients of a concentrator photovoltaic module. The apparatus includes a solar simulator for providing a radiant source, a environment chamber, a concentrator photovoltaic module, a temperature control unit for controlling the temperature of environment chamber, a circuit-voltage curve measurement unit for measuring current-voltage characteristics of a photovoltaic device and a reference cell for measuring the irradiation of the solar simulator.

7 Claims, 5 Drawing Sheets

_US 8,308,351 B2_

APPARATUS FOR MEASURING THE TEMPERATURE COEFFICIENT OF A CONCENTRATOR PHOTOVOLTAIC MODULE

CROSS REFERENCE TO RELATED PATENT APPLICATIONS

This application claims priority from Taiwan Patent Application No. 098136795, filed in the Taiwan Patent Office on Oct. 30, 2009, entitled "Apparatus for Measuring the Temperature Coefficients of a Concentrator Photovoltaic Module," and incorporates the Taiwan patent application in its entirety by reference.

TECHNICAL FIELD

The present disclosure relates to an indoor measurement apparatus for measuring the temperature coefficients of a concentrator photovoltaic module.

DESCRIPTION OF THE RELATED ART

Photovoltaic modules for converting the solar energy into electricity gets more attention as the fossil fuels are gets more expensive. The prices of the photovoltaic modules are determined by photo-electric conversion efficiencies and photovoltaic characteristics. The photovoltaic characteristics of a concentrator photovoltaic module are determined by its temperature coefficients. The temperature coefficients are the most important performance parameters of the power output related to the temperature. The photovoltaic characteristics of a concentrator photovoltaic module can be calculated from the temperature coefficients.

There has not been any indoor measurement apparatus specifically devised to measure the temperature coefficients of a concentrator photovoltaic module. Typically, for outdoor tests, the apparatus including a solar tracker, a current-voltage curve measuring unit and a temperature measuring unit is used to measure the temperature coefficients of a concentrator photovoltaic module.

The above-mentioned apparatus is limited by outdoor climatic conditions although it can measure the temperature coefficients of a concentrator photovoltaic module. Moreover, it is difficult to control the temperature of a concentrator photovoltaic module. It is more difficult to control the uniform temperature distribution of a concentrator photovoltaic module. Therefore, the precision of the measurement is bad.

The present disclosure is therefore intended to obviate or at least alleviate the problems encountered in prior art.

SUMMARY OF THE DISCLOSURE

It is the primary objective of the present disclosure to provide an apparatus for precisely measuring the temperature coefficients of a concentrator photovoltaic module.

To achieve the foregoing objective of the present disclosure, the apparatus includes a solar simulator, an environment chamber, a temperature controller, a reference cell and a measuring unit. The solar simulator emits collimated light in imitation of the sun light. The environment chamber includes a case, a gate, at least one door and a holder. The case includes front and rear openings. The gate is operable to close the front opening of the case before the temperature of the interior of the case reaches a desired value. The gate is operable to open the front opening of the case to allow the collimated light to reach the concentrator photovoltaic module after the temperature of the interior of the case reaches the desired value. The door is operable to open the rear opening through which the concentrator photovoltaic module is located in the case and closing the rear opening of the case before the temperature of the interior of the case reaches the desired value. The holder is located in the case and operable to hold the concentrator photovoltaic module. The temperature controller is connected to the case. The reference cell is located in the case. The measuring unit includes a first cable electrically connected to the concentrator photovoltaic module and a second cable electrically connected to the reference cell.

Other objectives, advantages and features of the present disclosure will become apparent from the following description referring to the attached drawings.

BRIEF DESCRIPTIONS OF THE DRAWINGS

The present disclosure will be described via detailed illustration of the preferred embodiment referring to the drawings wherein.

DESCRIPTION OF THE PREFERRED EMBODIMENT

Figure 1:
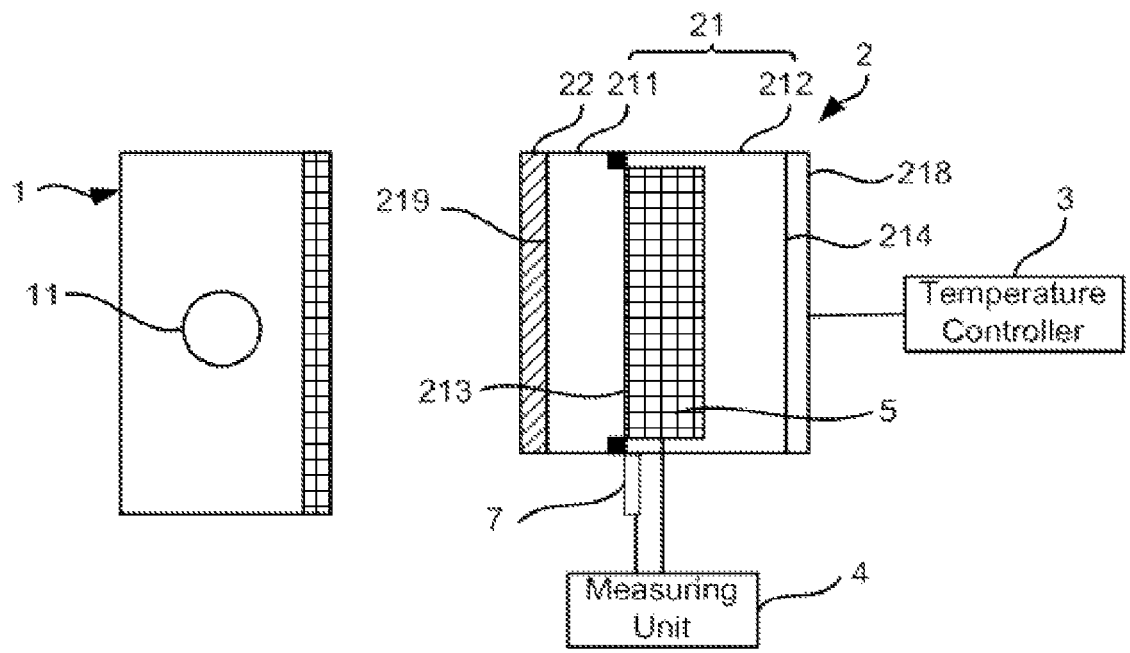
FIG. 1 is a cross-sectional view of an apparatus for measuring the temperature coefficients of a concentrator photovoltaic module according to the preferred embodiment of the present disclosure.
Figure 5:
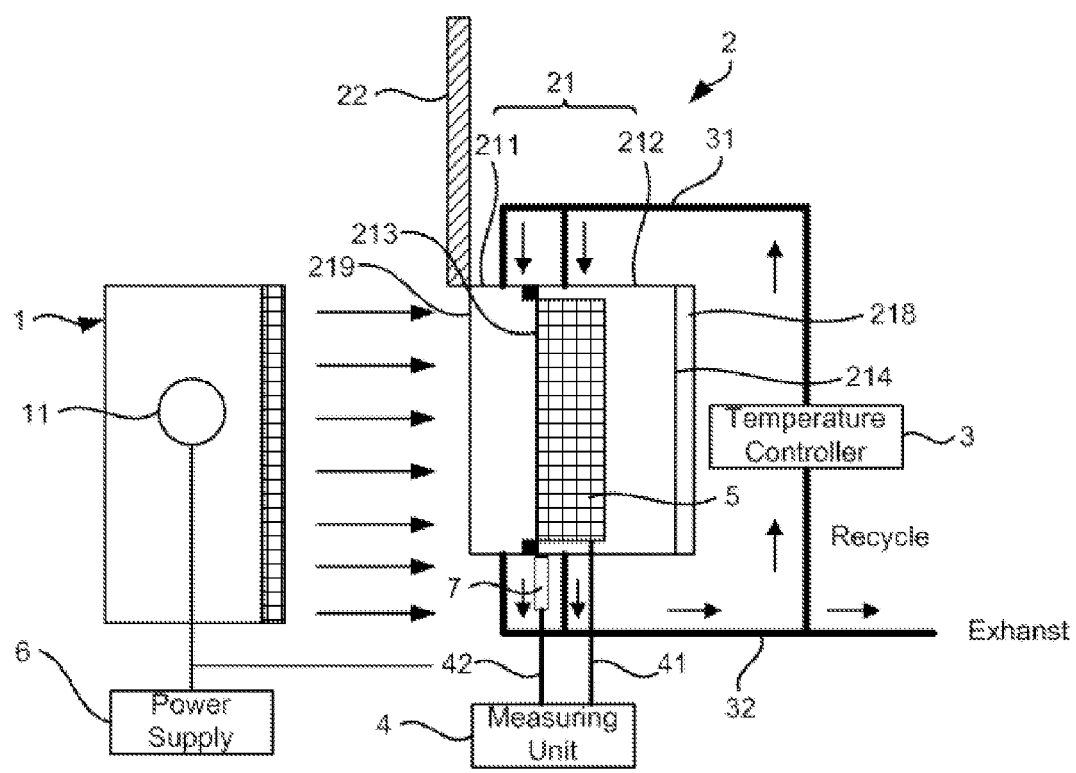
FIG. 5 is another cross-sectional view of the apparatus shown in FIG. 1 in operation.

Referring to FIGS. 1 and 5, there is shown an apparatus for measuring the temperature coefficients of a concentrator photovoltaic module 5 according to the present disclosure. The apparatus includes a solar simulator 1, an environment controller 2, a temperature controller 3, a measuring unit 4, a power supply 6 and a reference cell 7.

The solar simulator 1 includes a light 11. The light 11 emits collimated light in imitation of the sun light.

Figure 2:
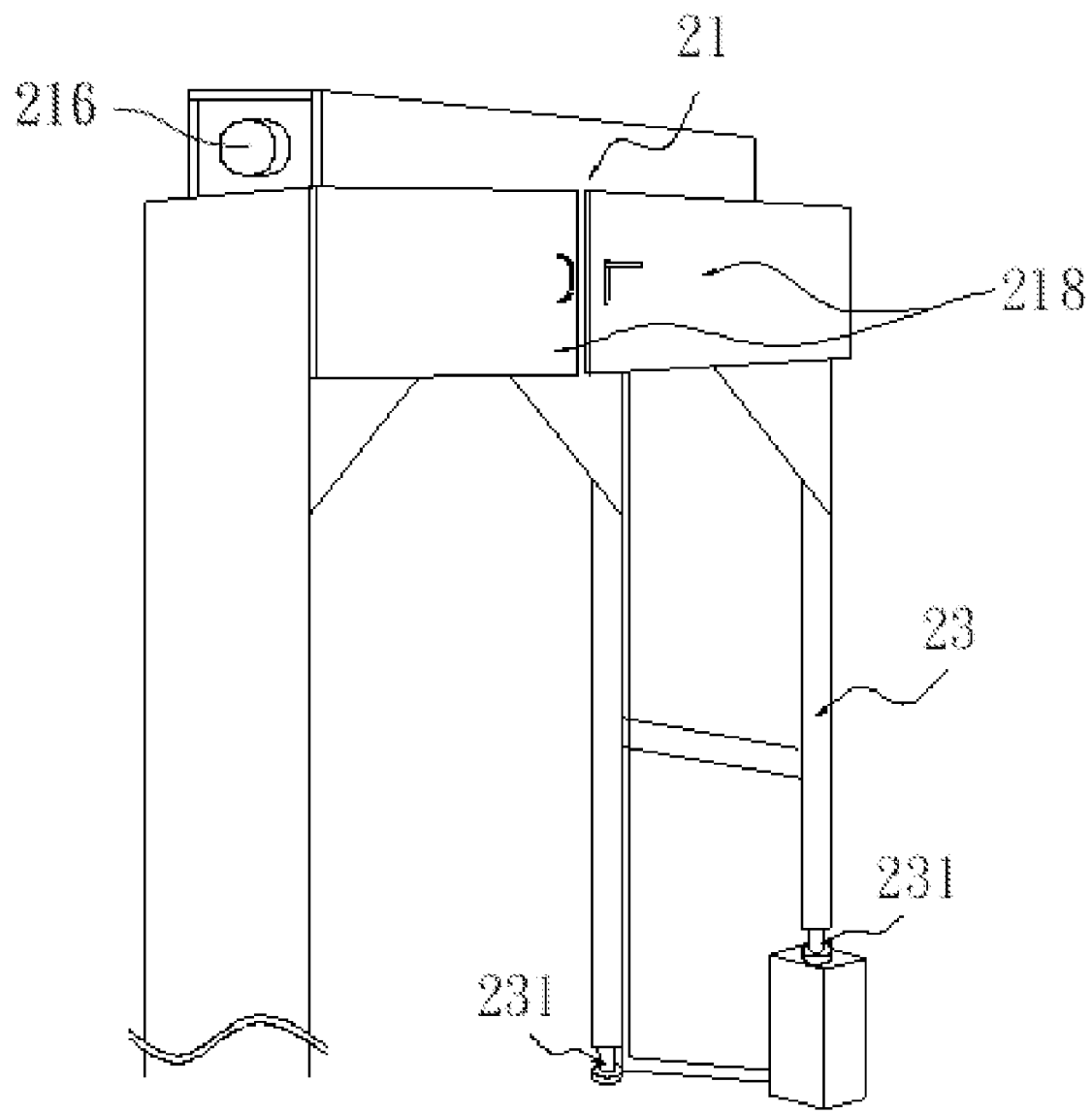
FIG. 2 is a perspective view of an environment chamber of the apparatus shown in FIG. 1.
Figure 3:
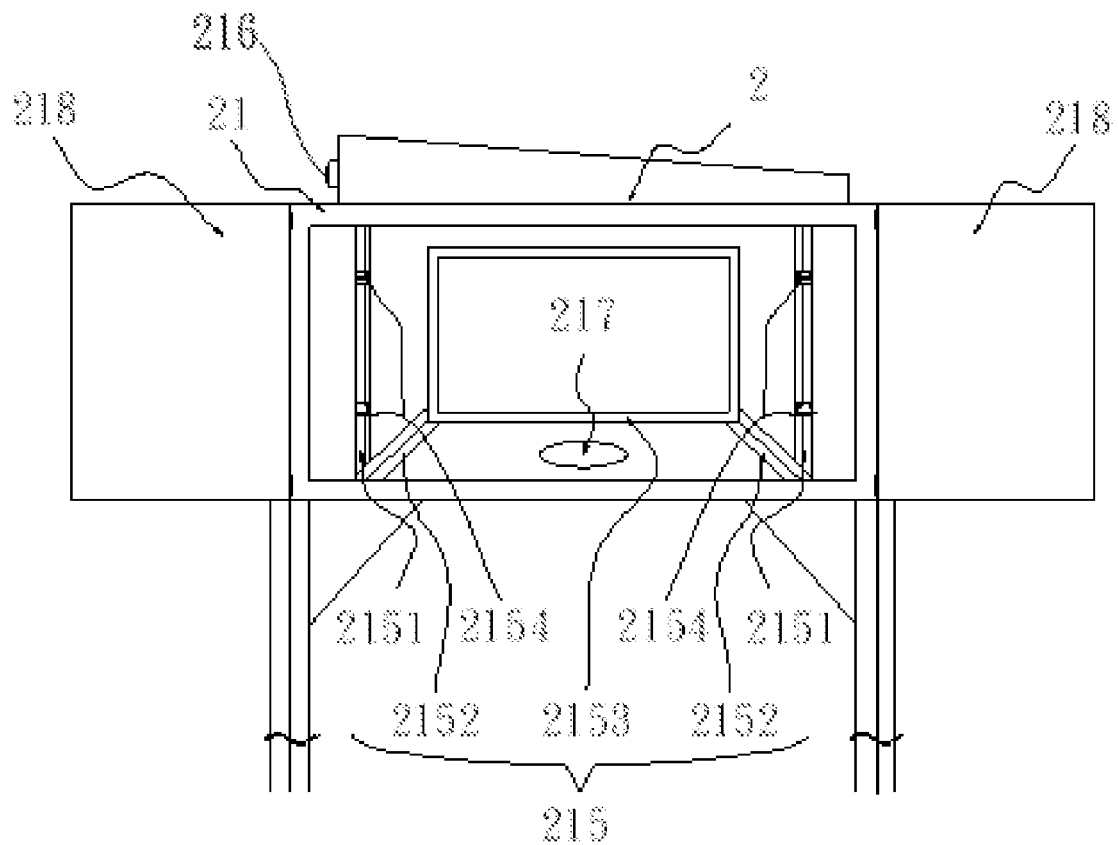
FIG. 3 is an enlarged front view of the environment chamber shown in FIG. 2.
Figure 4:
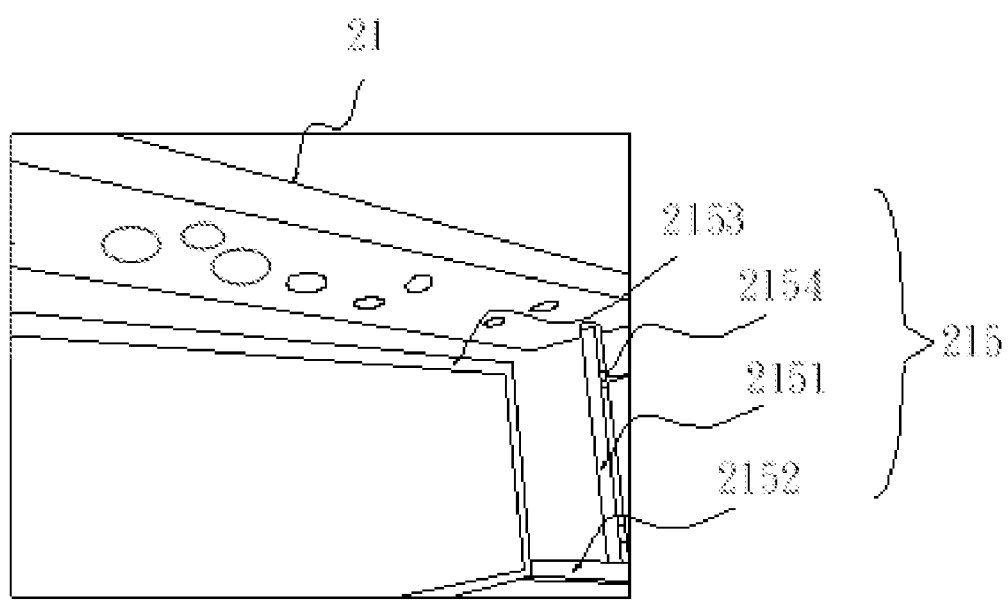
FIG. 4 is a perspective view of the environment chamber shown in FIG. 3.

Further referring to FIGS. 2 through 4, the environment chamber 2 includes a case 21 supported on a stand 23. The case 21 includes a front opening 219, a rear opening 214, a front chamber 211, a rear chamber 212 and a opening 213. The opening 213 is located between the front chamber 211 and the rear chamber 212. The area of the opening 213 is smaller than that of the front and rear openings 219, 214. The front chamber 211 and the rear chamber 212 are located between the front opening 219 and the rear opening 214. An inlet 216 is defined in a roof of the case 21. An outlet 217 is defined in a floor of the case 21.

A gate 22 is movably provided on the case 21. The gate 22 closes and opens the front opening of the case 21. Two doors 218 are pivotally connected to the case 21. The doors 218 close and open the rear opening 214 of the case 21.

A holder 215 is located in the front chamber 211. The holder 215 includes two posts 2151 extending from an internal face of the case 21, a frame 2153 and two corner rods 2151 each extending to a corner of the frame 2153 from the root of a related one of the posts 2151. Each of the posts 2151 has at least one fastener 2154.

The stand 23 includes retractable feet 231. The length of each of the retractable feet 231 is adjustable independent of the others. The stand 23 can thus support the case 21 on different torrential shapes of the ground.

The temperature controller 3 includes a heater and cooler (not shown) to provide different temperature of air, a first pipe 31 and a second pipe 32. The heater can be a hot wire that converts electricity into heat. The first pipe 31 sends hot or cold air into the case 21 via the inlet 216. The second pipe 32 returns the air thereto temperature controller 3 or exhaust from the case 21 through the outlet 217.

The measuring unit 4 includes a first cable 41 and a second cable 42. The first cable 41 is electrically connected to the concentrator photovoltaic module 5 and the second cable 42 is electrically connected to the reference cell 7.

The reference cell 7 is also located in the case 21. A front face of the reference cell 7 is in a same plane with a front face of the concentrator photovoltaic module 5.

In operation, the front opening of the case 21 is closed by the gate 22. The rear opening 214 of the case 21 is opened by operating the doors 218. The concentrator photovoltaic module 5 is located in the rear chamber 212 through the rear opening 214. The concentrator photovoltaic module 5 is supported on the frame 2153 and kept there by the fasteners 2154. The rear opening 214 of the case 21 is closed by the doors 218.

The desired air is sent into the case 21 from the temperature controller 3 through the first pipe 36 and the inlet 216. The air heats or cools the interior of the case 21 and the concentrator photovoltaic module 5. The air is sent back into the temperature controller 3 from the case 21 through the outlet 217 and the second pipe 32. Thus, the air is circulated or exhausted and heated or cooled. Accordingly, the temperature of the concentrator photovoltaic module 5 can be increased or decreased to a desired value. The humidity in the case 21 can also be controlled.

The front opening of the case 21 is opened by operating the gate 22. The light 11 emits collimated light to the front face of the concentrator photovoltaic module 5 and the front face of the reference cell 7. The measuring unit 4 measures the current and voltage curve of the concentrator photovoltaic module 5 relative to the reference cell 7. Furthermore, the measuring unit 4 calculates and shows other characteristics including the open-circuit voltage, the short-circuit current, the maximum-power voltage, the maximum-power current, the maximum power, fill factor and efficiency. The power supply 6 is operable to adjust the intensity of the collimated light emitted from the light 11.

With the apparatus of this disclosure, the photovoltaic characteristics of the concentrator photovoltaic module 5 at different temperatures can be measured while the uniformity of the temperature in concentrator photovoltaic module 5 is good. Thus, the temperature coefficient of the concentrator photovoltaic module 5 can be calculated.

The present disclosure has been described via the detailed illustration of the preferred embodiment. Those skilled in the art can derive variations from the preferred embodiment without departing from the scope of the present disclosure. Therefore, the preferred embodiment shall not limit the scope of the present disclosure defined in the claims.

What is claimed is:

1. An apparatus for measuring the temperature coefficient of a concentrator photovoltaic module, the apparatus comprising:
   a solar simulator for emitting collimated light which simulates the sun light;
   an environment chamber including:
      a case with front opening and rear opening;
      a gate operable to close the front opening of the case before the temperature of the interior of the case reaches a desired value and open the front opening of the case to allow the collimated light to reach the concentrator photovoltaic module located in the case after the temperature of the interior of the case reaches the desired value;
      at least one door operable to open the rear opening through which the concentrator photovoltaic module is located in the case and close the rear opening of the case before the temperature of the interior of the case reaches the desired value; and
      a holder located in the case and operable to hold the concentrator photovoltaic module;
   a temperature controller connected to the case;
   a reference cell located in the case;
   a measuring unit including a first cable electrically connected to the concentrator photovoltaic module and a second cable electrically connected to the reference cell.

2. The apparatus according to claim 1, wherein the case includes an inlet, wherein the temperature controller includes a first pipe for sending hot or cold air into the case via the inlet.

3. The apparatus according to claim 2, wherein the case includes an outlet, wherein the temperature controller includes a second pipe for returning the air into temperature controller from the case through the outlet.

4. The apparatus according to claim 1, wherein the holder includes two posts located in the case, a frame for supporting the concentrator photovoltaic module, and two corner rods each extending to a corner of the frame from a related one of the posts.

5. The apparatus according to claim 4, wherein the holder includes two fasteners operable for keeping the concentrator photovoltaic module on the frame.

6. The apparatus according to claim 4, wherein the case includes front and rear chambers and a opening between the front and rear chambers, wherein the frame is located in the opening.

7. The apparatus according to claim 6, wherein the area of the front and rear chambers is larger than that of the opening.

* * * * *